United States Patent
Zhan et al.

(10) Patent No.: US 12,336,853 B2
(45) Date of Patent: Jun. 24, 2025

(54) MOBILE DR APPLICABLE TO IN-VIVO DETECTION OF MULTI-THORACOLUMBAR VARIATIONS IN EQUINE ANIMALS AND USE METHOD

(71) Applicant: Liaocheng University, Liaocheng (CN)

(72) Inventors: Yandong Zhan, Liaocheng (CN); Changfa Wang, Liaocheng (CN); Yuhua Li, Liaocheng (CN); Ruitao Zhang, Liaocheng (CN); Zhenwei Zhang, Liaocheng (CN); Ziwen Liu, Liaocheng (CN); Mengmeng Li, Liaocheng (CN); Lanjie Li, Liaocheng (CN); Ying Han, Liaocheng (CN); Qingshan Ma, Liaocheng (CN); Liangliang Li, Liaocheng (CN); Wenqiong Chai, Liaocheng (CN); Yan Li, Liaocheng (CN); Tongtong Wang, Liaocheng (CN); Tao Jia, Liaocheng (CN); Jimin Jia, Liaocheng (CN); Shishuai Xing, Liaocheng (CN); Guiqin Liu, Liaocheng (CN); Wenqiang Liu, Liaocheng (CN); Mingxia Zhu, Liaocheng (CN); Miaomiao Zhou, Liaocheng (CN); Wei Zhang, Liaocheng (CN); Jingya Xing, Liaocheng (CN); Jinpeng Wang, Liaocheng (CN); Yan Sun, Liaocheng (CN)

(73) Assignee: LIAOCHENG UNIVERSITY, Liaocheng (CN)

( * ) Notice: Subject to any disclaimer, the term of this patent is extended or adjusted under 35 U.S.C. 154(b) by 427 days.

(21) Appl. No.: 17/976,007

(22) Filed: Oct. 28, 2022

(65) Prior Publication Data

US 2023/0210255 A1 Jul. 6, 2023

(30) Foreign Application Priority Data

Jan. 5, 2022 (CN) .......................... 202210005377.0

(51) Int. Cl.
*A61B 6/04* (2006.01)
*A61B 6/00* (2006.01)
*A61B 6/50* (2024.01)

(52) U.S. Cl.
CPC ............ *A61B 6/508* (2013.01); *A61B 6/0421* (2013.01); *A61B 6/4435* (2013.01); *A61B 6/505* (2013.01); *A61B 2503/40* (2013.01)

(58) Field of Classification Search
CPC ..... A47B 13/081; A47B 37/00; A61B 6/4405; A61B 6/505; A61B 6/508; A61B 6/5241;
(Continued)

(56) References Cited

U.S. PATENT DOCUMENTS

2016/0361036 A1* 12/2016 Ray .................... A61B 6/032
2018/0055467 A1*  3/2018 Cox .................... A61B 6/4458

* cited by examiner

*Primary Examiner* — David P Porta
*Assistant Examiner* — Mamadou Faye
(74) *Attorney, Agent, or Firm* — KRIEGSMAN & KRIEGSMAN

(57) ABSTRACT

A mobile DR applicable to in-vivo detection of multi-thoracolumbar variations in equine animals and a use method are provided. The DR mainly comprises four aspects: (1) a digital flat-panel X-ray imaging system; (2) equine animal retaining device system (radiography bed) applicable to different body sizes; (3) radiography parameters applicable to equine animals of different body sizes and at different developmental stages; and (4) a stitching system Polaris for radiographed pictures. The digital flat-panel X-ray imaging system comprises an X-ray tube, a beam limiting device, a high-voltage generator, a flat-panel detector, an image acquisition workstation.

5 Claims, 2 Drawing Sheets

(58) Field of Classification Search
CPC ..... A61B 6/544; A61B 6/0407; A61B 6/4429; A61B 6/4021; A61B 6/4452; A61B 6/4476; A61B 2503/40
See application file for complete search history.

MOBILE DR APPLICABLE TO IN-VIVO DETECTION OF MULTI-THORACOLUMBAR VARIATIONS IN EQUINE ANIMALS AND USE METHOD

CROSS REFERENCE TO RELATED APPLICATION

This patent application claims the benefit and priority of Chinese Patent Application No. 202210005377.0, filed on Jan. 5, 2022, the disclosure of which is incorporated by reference herein in its entirety as part of the present application.

TECHNICAL FIELD

The present disclosure relates to the technical field of DR (Digital Radiography), and in particular relates to a mobile DR applicable to in-vivo detection of multi-thoracolumbar variation in equine animals and a use method.

BACKGROUND ART

In livestock, there is an increase in the number of thoracic and lumbar vertebrae in some individuals compared to other individuals of the same species. The increase of thoracic-lumbar vertebral number will result in the lengthening of body size, the increase of the carcass length, and the corresponding increase of the meat yield, of the animals, thus improving their economic value. In-vivo detection and breeding for vertebral number traits, especially the breeding for multi-thoracolumbar variation, are of great economic importance for the breeding of livestock. However, there is no equipment and method applicable to in-vivo detection of multi-thoracolumbar variations in equine animals in China and at abroad. Based on this, equipment and method applicable to in-vivo detection of multi-thoracolumbar variations in equine animals are provided. The equipment mainly comprises four aspects: (1) a digital flat-panel X-ray imaging system; (2) equine animal retaining device system (radiography bed) applicable to different body sizes; (3) radiography parameters applicable to equine animals of different body sizes and at different developmental stages; and (4) a stitching system Polaris for radiographed pictures.

DR (Digital Radiography, direct digital flat-panel X-ray imaging system) refers to the technology of direct digital X-ray radiography under computer control. That is, the amorphous silicon flat-panel detector is used to convert X-ray information penetrating through the living body into a digital signal, and the computer is used to reconstruct an image and perform a series of image processing. The DR system mainly includes an X-ray generation device, a direct conversion flat-panel detector, a system controller, an impact monitor, an image processing workstation and other components, which is widely used in hospitals, veterinary hospitals and the like.

At present, in the hospital, the DR is fixed in a specific room, when used to radiograph the human body, due to good compliance of human, images can be easily stitched into a whole whether a specific part of the body is radiographed or the body is partly radiographed by the DR. In the pet hospital, the DR is usually used to radiograph small animals or a certain part of a large animal, and the detected animal needs to be anesthetized during use. However, the existing stage of fixed DR cannot meet the needs of different scenes due to its immovability, and a portable DR cannot meet the radiography needs for in-vivo detection of multi-thoracolumbar variations in equine animals for multi-vertebral number breeding due to its small power.

SUMMARY

An objective of the present disclosure is to provide equipment applicable to in-vivo detection of multi-thoracolumbar variations in equine animals and a use method. The equipment has the advantages of being convenient to move and convenient for the use of the equine animals, and solves the problems that the existing stage of fixed DR cannot meet the needs of different scenes due to its immovability, and an existing portable DR cannot meet the in-vivo radiography needs for multi-vertebral number breeding of large livestock due to its low power.

To achieve the objective, the present disclosure provides the following solutions: a mobile DR applicable to in-vivo detection of multi-thoracolumbar variations in equine animals. The DR mainly comprises four aspects: The DR mainly comprises four aspects: (1) a digital flat-panel X-ray imaging system; (2) equine animal retaining device system (radiography bed) applicable to different body sizes; (3) radiography parameters applicable to equine animals of different body sizes and at different developmental stages; and (4) a stitching system Polaris for radiographed pictures. The DR comprises a base plate, wherein supporting rods are fixedly connected to the periphery of the top of the base plate, and a sliding rail layer is fixedly connected to the lower parts of the supporting rods; the sliding rail layer comprises a fixed plate and a sliding rail, the sliding rail is fixedly mounted at the top of the fixed plate, and a sliding table is slidingly connected to the outer surface of the sliding rail; lift type telescopic arms are fixedly connected to the left end and the right end of the top of the sliding table; an X-ray receiving flat panel is fixedly mounted at the top of the lift type telescopic arm at the left end of the top of the sliding table, and an X-ray tube is fixedly connected to the top of the lift type telescopic arm at the right end of the top of the sliding table; a partition is fixedly connected to the lower parts of the supporting rods and located at the upper part of the sliding table; retaining frames are fixedly connected to the left end and the right end of the top of the partition, and a leg stop lever is provided between the two retaining frames; and a transverse retainer is slidingly connected between the left supporting rod and the right supporting rod at the top of the base plate, and a longitudinal retainer is slidingly connected to the top of the transverse retainer.

Preferably, the number of transverse retainers is two, and the partition is provided with wooden ramps at the front end and the rear end.

Preferably, the right end of the top of the fixed plate is provided with a plurality of through holes, a sliding rail lock is movably connected to the right end of the sliding table, and the bottom of the sliding rail block penetrates through the sliding table and extends to an inner cavity of the through hole.

Preferably, stop levers are provided between the front supporting rod and the rear supporting rod at the top of the base plate, and the number of the stop levers is two.

Preferably, a plurality of longitudinal plates are fixedly connected to the bottom of the base plate, each longitudinal plate having a height of 12 cm to 15 cm.

Compared with the prior art, the present disclosure has the following beneficial effects:

The X-ray receiving flat panel and the X-ray tube can be driven, by the lift type telescopic arms, to move up and down, thus facilitating the people to radiograph during the in-vivo detection of multi-thoracolumbar variations in equine animals at different age groups and of different body sizes. The X-ray receiving panel and the X-ray tube can be driven, by the sliding rail layer and the sliding table, to move back and forth, facilitating to radiograph different parts in the in-vivo detection of multi-thoracolumbar variations in equine animals. The transverse retainer, the longitudinal retainer and the stop levers are used to retain the livestock of different body sizes. The base plate and the longitudinal plate are used to facilitate a forklift or pallet truck to support the equipment up and down a transport vehicle, which can make the DR move along with the vehicle and facilitates the people to move this device. The partition can be used to prevent the excrements of the livestock from falling on the sliding rail layer. The problems that the existing stage of fixed DR cannot meet the needs of different scenes due to its immovability, and a portable DR cannot meet the radiography needs for in-vivo detection of multi-thoracolumbar variations in equine animals for multi-vertebral number breeding due to its small power are solved.

BRIEF DESCRIPTION OF THE DRAWINGS

The accompanying drawings illustrated herein are used to provide a further understanding of the present disclosure and constitute part of the present disclosure. The schematic embodiments of the present disclosure and the description thereof are used to explain the present disclosure and do not constitute an undue limitation of the present disclosure. In the drawings.

Figure 1:
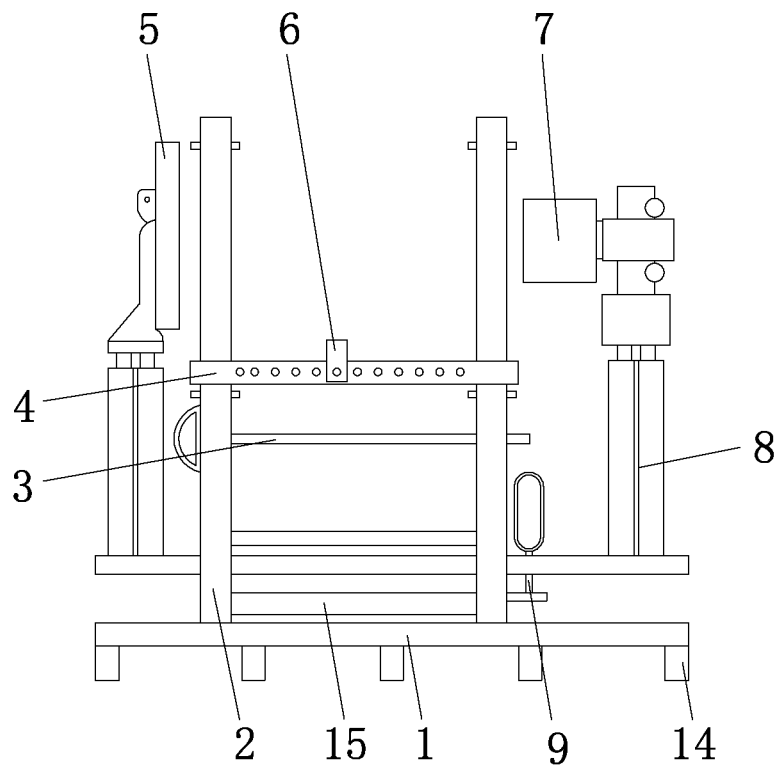
FIG. 1 is a schematic diagram of a structure according to the present disclosure.

In the drawings: 1—base plate; 2—supporting rod; 3—leg stop lever; 4—transverse retainer; 5—X-ray receiving flat panel; 6—longitudinal retainer; 7—X-ray tube; 8—lift type telescopic arm; 9—sliding rail lock; 10—stop lever; 11—retaining frame; 12—sliding table; 13—partition; 14—longitudinal plate; 15—sliding rail layer.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

In the description of the present disclosure, it needs to be noted that, unless expressly specified and limited otherwise, the terms "mounted", "disposed", "connection" and the like should be understood broadly, e.g., either fixed connection, detachable connection, or integral connection; either mechanical connection or electrical connection; either direct connection or indirect connection via an intermediate medium; either internal communication of two elements or an interaction relationship between the two elements. To those of ordinary skill in the art, the specific meaning of the above terms in the present disclosure can be understood in specific cases.

A base plate 1, supporting rods 2, leg stop levers 3, a transverse retainer 4, an X-ray receiving flat panel 5, a longitudinal retainer 6, an X-ray tube 7, lift type telescopic arms 8, a sliding rail lock 9, a stop lever 10, a retaining frame 11, a sliding table 12, a partition 12, a longitudinal plate 14, and a sliding rail layer 5 are common standard components or components known to those skilled in the art, the structure and principle of which can be known to those skilled in the art through technical manuals or through conventional experimental methods.

Figure 2:
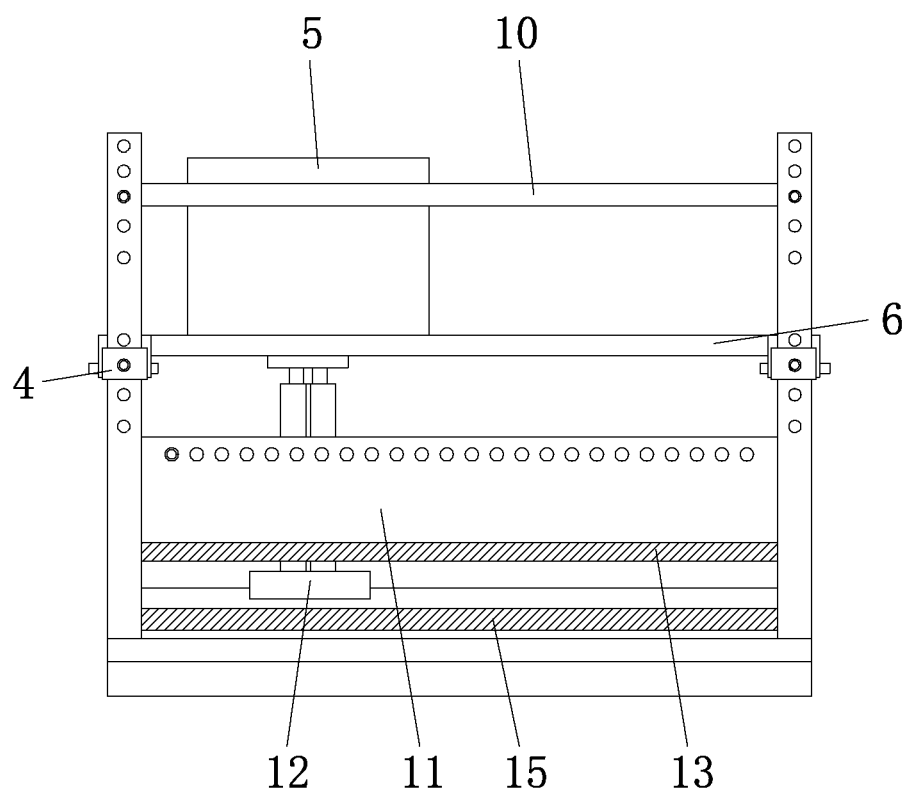
FIG. 2 is a schematic diagram of a sectional structure in a right-view state according to the present disclosure.

Please refer to FIG. 1 to FIG. 2, a mobile DR applicable to in-vivo detection of multi-thoracolumbar variations in equine animals is provided. The DR comprises a base plate 1, wherein supporting rods 2 are fixedly connected to the periphery of the top of the base plate 1, and a sliding rail layer 15 is fixedly connected to the lower parts of the supporting rods 2; the sliding rail layer 15 comprises a fixed plate and a sliding rail, the sliding rail is fixedly mounted at the top of the fixed plate, and a sliding table 12 is slidingly connected to the outer surface of the sliding rail; lift type telescopic arms 8 are fixedly connected to the left end and the right end of the top of the sliding table 12; an X-ray receiving flat panel 5 is fixedly mounted at the top of the lift type telescopic arm 8 at the left end of the top of the sliding table 12, and an X-ray tube 7 is fixedly connected to the top of the lift type telescopic arm 8 at the right end of the top of the sliding table 12; a partition 13 is fixedly connected to the lower parts of the supporting rods 12 and located at the upper part of the sliding table 12; retaining frames 11 are fixedly connected to the left end and the right end of the top of the partition 13, and a leg stop lever 3 is provided between the two retaining frames 11; and a transverse retainer 4 is slidingly connected between the left supporting rod 2 and the right supporting rod 2 at the top of the base plate, and a longitudinal retainer 6 is slidingly connected to the top of the transverse retainer 4. The number of transverse retainers 4 is two, and the partition 13 is provided with wooden ramps at the front end and the rear end. The right end of the top of the fixed plate is provided with a plurality of through holes, a sliding rail lock 9 is movably connected to the right end of the sliding table 12, and the bottom of the sliding rail block 9 penetrates through the sliding table 12 and extends to an inner cavity of the through hole. Stop levers 10 are provided between the front supporting rod 2 and the rear supporting rod 2 at the top of the base plate 1, and the number of the stop levers 10 is two. A plurality of longitudinal plates 14 are fixedly connected to the bottom of the base plate 1, each longitudinal plate 14 having a height of 12 cm to 15 cm. The X-ray receiving flat panel 5 and the X-ray tube 7 can be driven, by the lift type telescopic arms 8, to move up and down, thus facilitating the people to radiograph during the in-vivo detection of multi-thoracolumbar variations in equine animals at different age groups and of different body sizes. The X-ray receiving panel 5 and the X-ray tube 7 can be driven, by the sliding rail layer 15 and the sliding table 12, to move back and forth, facilitating to radiograph different parts in the in-vivo detection of multi-thoracolumbar variations in equine animals. The transverse retainer 4, the longitudinal retainer 6 and the stop levers 10 are used to retain the livestock of different body sizes. The base plate 1 and the longitudinal plate 14 are used to facilitate a forklift or pallet truck to support the equipment up and down a transport vehicle, which can make the DR move along with the vehicle and facilitates the people to move this device. The partition 13 can be used to prevent the excrements of the livestock from falling on the sliding rail layer 15. The problems that the existing stage of fixed DR cannot meet the needs of different scenes due to its immovability, and a portable DR cannot meet the radiography needs for in-vivo detection of multi-thoracolumbar variations in equine animals for multi-vertebral number breeding due to its small power are solved.

During use of a mobile DR applicable to in-vivo detection of multi-thoracolumbar variations in equine animals, the X-ray receiving flat panel 5 and the X-ray tube 7 can be driven, by the lift type telescopic arms 8, to move up and down, thus facilitating the people to radiograph during the in-vivo detection of multi-thoracolumbar variations in equine animals at different age groups and of different body sizes. The X-ray receiving panel 5 and the X-ray tube 7 can be driven, by the sliding rail layer 15 and the sliding table 12, to move back and forth, facilitating to radiograph different parts in the in-vivo detection of multi-thoracolumbar variations in equine animals. The transverse retainer 4, the longitudinal retainer 6 and the stop levers 10 are used to retain the livestock of different body sizes. The base plate 1 and the longitudinal plate 14 are used to facilitate a forklift or pallet truck to support the equipment up and down a transport vehicle, which can make the DR move along with the vehicle and facilitates the people to move this device. The partition 13 can be used to prevent the excrements of the livestock from falling on the sliding rail layer 15. The problems that the existing stage of fixed DR cannot meet the needs of different scenes due to its immovability, and a portable DR cannot meet the radiography needs for in-vivo detection of multi-thoracolumbar variations in equine animals for multi-vertebral number breeding due to its small power are solved.

Although the embodiments of the present disclosure have been shown and described, those of ordinary skill in the art may appreciates that various changes, modifications, substitutions and variations may be made to theses embodiments without departing from the principles and spirit of the present disclosure, the scope of the present disclosure is defined by the appended claims and their equivalents.

What is claimed is:

1. A mobile DR applicable to in-vivo detection of multi-thoracolumbar variations in equine animals, comprising a base plate (1), wherein supporting rods (2) are fixedly connected to a periphery of a top of the base plate (1), and a sliding rail layer (15) is fixedly connected to lower parts of the supporting rods (2); the sliding rail layer (15) comprises a fixed plate and a sliding rail, the sliding rail is fixedly mounted at a top of the fixed plate, and a sliding table (12) is slidingly connected to an outer surface of the sliding rail; lift type telescopic arms (8) are fixedly connected to a left end and a right end of a top of the sliding table (12); an X-ray receiving flat panel (5) is fixedly mounted at a top of the lift type telescopic arm (8) at the left end of the top of the sliding table (12), and an X-ray tube (7) is fixedly connected to the top of the lift type telescopic arm (8) at the right end of the top of the sliding table (12); a partition (13) is fixedly connected to lower parts of the supporting rods (2) and located at an upper part of the sliding table (12); two retaining frames (11) are separately fixedly connected to a left end and a right end of a top of the partition (13), and a leg stop lever (3) is provided between the two retaining frames (11); and a transverse retainer (4) is slidingly connected between a left supporting rod of the supporting rods (2) and a right supporting rod of the supporting rods (2) at the top of the base plate, and a longitudinal retainer (6) is slidingly connected to a top of the transverse retainer (4).

2. The mobile DR applicable to in-vivo detection of multi-thoracolumbar variations in equine animals according to claim 1, wherein there are two transverse retainers (4), and the partition (13) is provided with wooden ramps at a front end and a rear end.

3. The mobile DR applicable to in-vivo detection of multi-thoracolumbar variations in equine animals according to claim 1, wherein a right end of the top of the fixed plate is provided with a plurality of through holes, a sliding rail lock (9) is movably connected to a right end of the sliding table (12), and a bottom of the sliding rail block (9) penetrates through the sliding table (12) and extends to an inner cavity of one of the plurality of through holes.

4. The mobile DR applicable to in-vivo detection of multi-thoracolumbar variations in equine animals according to claim 1, wherein stop levers (10) are provided between a front supporting rod of the supporting rods (2) and a rear supporting rod of the supporting rods (2) at the top of the base plate (1), and there are two stop levers (10).

5. The mobile DR applicable to in-vivo detection of multi-thoracolumbar variations in equine animals according to claim 1, wherein a plurality of longitudinal plates (14) are fixedly connected to a bottom of the base plate (1), each longitudinal plate (14) having a height of 12 cm to 15 cm.

* * * * *